(12) United States Patent
Hoess et al.

(10) Patent No.: US 7,232,577 B2
(45) Date of Patent: Jun. 19, 2007

(54) READILY DISPERSIBLE DIETARY FIBER COMPOSITION

(75) Inventors: Frank Hoess, Holland, MI (US); James McGinnis, Allegan, MI (US)

(73) Assignee: L. Perrigo Company, Allegan, MI (US)

( * ) Notice: Subject to any disclaimer, the term of this patent is extended or adjusted under 35 U.S.C. 154(b) by 585 days.

(21) Appl. No.: 10/274,803

(22) Filed: Oct. 21, 2002

(65) Prior Publication Data

US 2004/0076658 A1 Apr. 22, 2004

(51) Int. Cl.
*A61K 9/14* (2006.01)
*A61K 47/00* (2006.01)

(52) U.S. Cl. ...................... 424/489; 424/439

(58) Field of Classification Search ................ 424/439, 424/440, 441, 464, 489
See application file for complete search history.

(56) References Cited

U.S. PATENT DOCUMENTS

| 2,970,056 | A | | 1/1961 | Benson et al. |
|---|---|---|---|---|
| 3,715,216 | A | | 2/1973 | Wurhmann et al. |
| 3,812,269 | A | | 5/1974 | Mueller et al. |
| 3,975,547 | A | | 8/1976 | D'Ercole |
| 3,983,251 | A | | 9/1976 | Singh |
| 4,016,337 | A | | 4/1977 | Hsu |
| 4,232,052 | A | | 11/1980 | Nappen |
| 4,278,695 | A | | 7/1981 | Velasco |
| 4,288,460 | A | | 9/1981 | Ciliberto et al. |
| 4,357,260 | A | | 11/1982 | Sandford et al. |
| 4,459,280 | A | | 7/1984 | Colliopoulos et al. |
| 4,548,806 | A | * | 10/1985 | Colliopoulos et al. ...... 424/440 |
| 4,551,331 | A | | 11/1985 | Rudin |
| 4,565,702 | A | | 1/1986 | Morley et al. |
| 4,619,831 | A | | 10/1986 | Sharma |
| 4,619,833 | A | | 10/1986 | Anderson |
| 4,698,264 | A | | 10/1987 | Steinke |
| 4,758,440 | A | | 7/1988 | van der Heem |
| RE32,811 | E | | 12/1988 | Rudin |
| 4,814,172 | A | | 3/1989 | Chavkin et al. |
| 4,828,842 | A | | 5/1989 | Furst et al. |
| 4,867,902 | A | * | 9/1989 | Russell ................. 252/186.32 |
| 4,877,627 | A | | 10/1989 | Leitz et al. |
| 4,927,649 | A | | 5/1990 | Antenucci |
| 4,978,529 | A | | 12/1990 | Denick, Jr. |
| 5,085,883 | A | | 2/1992 | Garleb et al. |
| 5,102,682 | A | | 4/1992 | Nasrallah et al. |
| 5,118,510 | A | | 6/1992 | Kuhrts |
| 5,137,744 | A | | 8/1992 | Cagley et al. |
| 5,162,128 | A | | 11/1992 | Mills et al. |
| 5,219,570 | A | * | 6/1993 | Barbera ..................... 424/738 |
| 5,232,724 | A | | 8/1993 | Aldcroft et al. |
| 5,234,704 | A | | 8/1993 | Devine et al. |
| 5,294,457 | A | | 3/1994 | Jenkins et al. |
| 5,320,847 | A | | 6/1994 | Valentine et al. |
| 5,374,444 | A | | 12/1994 | Langner |
| 5,407,694 | A | | 4/1995 | Devine et al. |
| 5,490,997 | A | | 2/1996 | Devine et al. |
| 5,516,524 | A | * | 5/1996 | Kais et al. .................. 424/439 |
| 5,679,390 | A | | 10/1997 | Conover |
| 5,741,505 | A | | 4/1998 | Beyer et al. |
| 5,851,578 | A | | 12/1998 | Gandhi |
| 5,976,603 | A | | 11/1999 | Kota et al. |
| 6,066,341 | A | * | 5/2000 | Wilson ....................... 424/680 |
| 6,180,159 | B1 | | 1/2001 | Villagran et al. |
| 6,245,326 | B1 | * | 6/2001 | Topping et al. .......... 424/78.01 |
| 6,251,457 | B1 | | 6/2001 | Takaichi et al. |
| 6,290,997 | B1 | | 9/2001 | Villagran et al. |
| 6,303,167 | B1 | | 10/2001 | Morris et al. |
| 6,312,730 | B1 | | 11/2001 | Sander |
| 6,361,799 | B1 | * | 3/2002 | Palkhiwala ................. 424/489 |
| 2005/0089560 | A1 | * | 4/2005 | Daggy et al. ............... 424/464 |

* cited by examiner

*Primary Examiner*—Susan Tran
(74) *Attorney, Agent, or Firm*—Price, Heneveld, Cooper, DeWitt & Litton, LLP

(57) ABSTRACT

The present invention includes a dispersible dietary fiber composition comprising a colloidal silicon dioxide and a substantially uncoated, fibrous, vegetable material powder that is not naturally dispersible in water, which preferably includes psyllium. Other components, such as a saccharide polymer compound (preferably maltodextrin), a preservative, and a flavorant may also be included. The present invention further includes a method for producing a readily dispersible dry dietary fiber composition by dry blending colloidal silicon dioxide and a substantially uncoated, fibrous, vegetable material powder.

30 Claims, No Drawings

READILY DISPERSIBLE DIETARY FIBER COMPOSITION

BACKGROUND OF THE INVENTION

The present invention relates to bulk forming laxative products and methods for producing the same. These are typically based on psyllium or an equivalent fibrous vegetable material.

Such products typically include sugar, which facilitates dispersion of the fibrous vegetable material in water so that it can be consumed. However, dispersion continues to be and has for some time been a serious problem in sugar-free fibrous vegetable bulking products. The fibrous material simply does not disperse adequately in water.

U.S. Pat. No. 4,321,263 to Powell et al., issued Mar. 23, 1982, and entitled "PSYLLIUM COMPOSITIONS," wets the psyllium with a minimum of 2% of either polyethylene glycol or polyvinyl polyvinylpyrrolidone, and alleges that the resulting psyllium composition is substantially instantly dispersible in water.

Most prior art attempts, like the '263 patent, to formulate a dispersible dietary fiber composition have centered around coating the non-dispersible dietary fiber material with some type of dispersing agent. For example, U.S. Pat. No. 4,828,842, which is owned by the Assignee in this case, L. Perrigo Company, discloses a dietary bulking agent comprising psyllium powder, aspartame, and a coating of a blend of hydroxypropyl methylcellulose, with a minor amount of polyethylene glycol. Additionally, U.S. Pat. No. 4,016,337 discloses finely-divided particles of a normally non-dispersible material in a silicon dioxide flow agent having a thin coating of an emulsion of edible fat and glycerol. According to the '337 patent, the non-dispersible material is converted into an aqueous dispersion through the co-action of silicon dioxide flow agent and the emulsion of edible fat and glycerol. In U.S. Pat. No. 4,548,806, in order to improve dispersibility of psyllium hydrophilic mucilloid, a film of hydrolyzed starch oligosaccharide, a mono- or di-saccharide, a polyglucose, or a polymaltose coating is applied.

Accordingly, there is a significant need for a composition and method for making a dietary fiber composition of normally non-dispersible dietary fiber, where coating the non-dispersible dietary fiber is unnecessary. Such a method would eliminate many processing steps and inherent costs that result from prior art solutions requiring coatings.

SUMMARY OF THE INVENTION

In the dietary fiber and method of the present invention, a readily dispersible dietary fiber composition includes colloidal silicon dioxide; a substantially uncoated, fibrous, vegetable material powder that is not naturally dispersible in water; and optionally a saccharide polymer compound. Typically, the composition does not contain an emulsion of edible fat and glycerol.

These and other features, advantages and objects of the present invention will be further understood and appreciated by those skilled in the art by reference to the following specification, claims and appended drawings.

DETAILED DESCRIPTION OF THE PREFERRED EMBODIMENT

In the preferred embodiment, a dietary fiber composition of the present invention comprises a colloidal silicon dioxide compound, a substantially uncoated, fibrous, vegetable material powder, most preferably psyllium powder and optionally, a saccharide polymer compound, such as maltodextrin, a flavorant, and a preservative. Notably, no coating of the vegetable material powder is required to adequately disperse it in water when colloidal silicon dioxide is used in conjunction with it. While the saccharide polymer compound, the flavorant, and the preservative are not necessary, they may be added as desired. Applicants currently believe the colloidal silicon dioxide significantly enhances the dispersibility of the dietary fiber and allows uncoated dietary fiber to be used in the dietary fiber composition of the present invention resulting in significant processing cost savings.

Preferably, the method of making the above dietary fiber compositions is by dry mixing at least a colloidal silicon dioxide and a fibrous vegetable material powder that is not naturally dispersible in water. The other ingredients are also preferably dry mixed. The dry mixing of the present invention eliminates any need for coating the fibrous material resulting in substantial cost savings. The fact that substantially uncoated, fibrous, vegetable material powder that is not naturally dispersible in water may be dispersible by the addition of colloidal silicon dioxide is entirely unexpected.

The colloidal silicon dioxide of the present invention is preferably CAB-O-SIL® M-5 available from Cabot Corporation of Tuscola, Ill. CAB-O-SIL® M-5 is a synthetic, amorphous, colloidal silicon dioxide. The colloidal silicon dioxide of the present invention preferably typically has the following properties:

| Typical Properties of Colloidal Silicon Dioxide of the Present Invention | |
|---|---|
| B.E.T. Surface Area | 200 m$^2$/g |
| pH (4% aqueous slurry) | 3.7–4.3 |
| 325 Mesh Residue (44 microns) | 0.02% max. |
| Bulk Density (at time of packaging) (Pour Density) | 3.0 lb/ft$^3$ max. (50 g/l Tap Density) |
| Loss on Heating (at time of packaging) | <1.5% max. |
| Loss on Ignition (@ 1000° C.) (at time of packaging) | <2 wt. % |
| Specific Gravity | 2.2 g/cm$^3$ |
| Wt. per gallon | 18.3 lb |
| Refractive Index | 1.46 |
| X-ray Form | Amorphous |
| Assay (% SiO$_2$) | >99.8 |
| Oil Adsorption | ~350 g/100 g oil |
| Average Particle (Aggregate) Length | 0.2–0.3 microns |

Preferably, the dietary fiber composition of the present invention includes from about 0.5% to about 10% colloidal silicon dioxide powder by weight of the composition. More preferably, from about 1% to about 3% colloidal silicon dioxide may be employed, and most preferably, about 2% by weight colloidal silicon dioxide of the composition is utilized.

The preferred fibrous vegetable material is an indigestible powder, most preferably psyllium powder. Psyllium powder comprises the ground husks of the seeds of the plantago ovata plant species. The husks consist principally of the colorless epidermis of mucilage containing cells. Any similarly powdered fibrous vegetable material, which serves as a bulking agent and for which dispersion in water does not readily occur naturally, could also be used in the present invention. The preferred psyllium powder is less than about 20 mesh (U.S. Series Sieve) particle size. The dietary fiber preferably amounts to from about 55% to about 65% by weight of the composition, but most preferably is about 60% by weight of the composition.

Optionally, the dietary fiber composition of the present invention further includes a saccharide polymer compound, preferably maltodextrin, as a filler. The maltodextrins consist of D-glucose units linked primarily by alpha-1,4 bonds with a dextrose equivalence (DE) of below 20. The maltodextrins used in the present invention generally fall between about 5 DE and about 20 DE. Typically, the maltodextrins have a dextrate equivalent of about 9–12 and most typically about 10. Applicants currently typically utilize maltodextrin sold under the designation MALTRIN® M510 by Grain Processing Corporation of Muscatine, Iowa.

Other optional ingredients that may be used in the present invention include flavorants, preferably sugar-free flavorants, such as aspartame, preservatives, and other compounds, such as citric acid. All of the optional ingredients are preferably dry.

The dietary fiber compositions of the present invention are further explained by the following examples:

EXAMPLE I

| Ingredient | Amount |
|---|---|
| Sugar-free fiber therapy mix of psyllium powder (Psyllium + all other ingredients desired, except CAB-O-SIL ®) | 100 grams |
| CAB-O-SIL ® M-5 | 1 gram |

Good dispersibility and taste was observed from the above composition. Only small lumps after 20 seconds remained.

EXAMPLE II

| Ingredient | Amount |
|---|---|
| Sugar-free fiber therapy mix of psyllium powder (Psyllium + all other ingredients desired, except CAB-O-SIL ®) | 100 grams |
| CAB-O-SIL ® M-5 | 2 grams |

Only small lumps were apparent after 20 seconds. The mix had good taste and was the best of Examples I and II.

EXAMPLE III

| 1% CAB-O-SIL ® M-5 composition employing flavorant and maltodextrin | | |
|---|---|---|
| Material | Percent by Weight | Amount |
| Sugar-free psyllium (ungranulated) | 59.84 | 1196.8 grams |
| Sugar-free orange flavorant | 7.46 | 149.2 grams |
| Maltodextrin M-510 | 31.70 | 634.0 grams |
| CAB-O-SIL ® M-5 | 1.00 | 20.0 grams |
| Total: | 100.00 | 2000.0 grams |

The composition of the above components were passed through a 20 mesh security screen and into a PK (Patterson-Kelley) blender and mixed for 10 minutes. The dispersion results were very good.

EXAMPLE IV

| 2% CAB-O-SIL ® M-5 composition employing flavorant and maltodextrin | | |
|---|---|---|
| Material | Percent by Weight | Amount |
| Sugar-free psyllium (ungranulated) | 59.84 | 1196.8 grams |
| Sugar-free orange flavorant | 7.46 | 149.2 grams |
| Maltodextrin M-510 | 30.70 | 614.0 grams |
| CAB-O-SIL ® M-5 | 2.00 | 40.0 grams |
| Total: | 100.00% | 2000.0 grams |

The composition of the above components were passed through a 20 mesh security screen and into a PK blender and mixed for 10 minutes. The dispersion results were very good.

EXAMPLE V

| 70 Kg Batch containing 2% by weight CAB-O-SIL ® M-5 | | |
|---|---|---|
| Material | Percent by Weight | Amount |
| Sugar-free psyllium (ungranulated) | 59.84 | 41.888 Kg |
| Sugar-free orange flavorant | 7.46 | 5.222 Kg |
| Maltodextrin M-510 | 30.70 | 21.490 Kg |
| CAB-O-SIL ® M-5 | 2.00 | 1.400 Kg |
| Total: | 100.00% | 70.000 Kg |

The composition of the above components were passed through a 20 mesh security screen and into a PK blender and mixed for 10 minutes. The dispersion results were very good.

To make the composition of Example V, the sugar-free orange flavorant in the CAB-O-SIL® M-5 were placed into a five cubic foot PK blender and mixed for five minutes. Next, that mixture was passed through a Fitzmill with knives forward at medium speed (approximately 2,450 rpm) with a 1531-0065 screen. Once complete, the processed mixture of CAB-O-SIL® M-5 and orange flavorant, the sugar-free psyllium dietary fiber mixture, and the maltodextrin were added into the five cubic foot PK blender and mixed for 10 minutes. Once mixed, the mixture of all the ingredients was placed in a suitable container.

Complete dispersibility tests were conducted by filling a glass beaker with 240 ml of water and placing one rounded teaspoon (approximately 5.8 gm) of the mixture into the filled glass bleaker and stirred. The mixture dispersed in less than six seconds. The color in the solution was slightly orange but nevertheless acceptable. The loose density of the mixture was approximately 0.58 and the tapped density was approximately 0.67 gm/mL.

The product produced containing 1% CAB-O-SIL® M-5 has the following properties:

| Determination | Product w/1% CAB-O-SIL ® M-5 |
|---|---|
| Selected Assay: | |
| aspartame, % by wt. | 0.60; acceptable |
| PH, (10 g/300 mL H$_2$O) | 3.0; acceptable |
| USP Swell Volume, mL (1) | 190; acceptable |
| Bulk Density, g/cm$^3$ | |
| Free Flow | 0.69 |
| Tapped | 0.74 |
| Organoleptic Evaluation | |
| Appearance, as is | Very fine tan powder with brown & orange specks |
| Color, in solution | Medium orange |
| Odor, in solution | Orange with very slight vegetable background |
| Flavor | Sweet, slightly tart orange |
| Mouthfeel | Very slightly gelatinous; acceptable |
| Dispersibility | Acceptable; mixes readily with brisk stirring |
| Product workmanship | Acceptable; no defects |

EXAMPLE VI

| Ingredient Name | Function | % of Formula | % wt/wt range | gm per dose |
|---|---|---|---|---|
| Psyllium Hydrophilic Mucilloid - (sugar-free) | Active | 48.0948 | 40–50 | 2.7895 |
| Psyllium Hydrophilic Mucilloid (sugar-free) | Active | 10.5431 | 10–20 | 0.6115 |
| Aspartame | Sweetening Agent | 0.6359 | <1 | 0.0369 |
| Citric Acid | Flavor | 5.7522 | 1–10 | 0.3336 |
| Colloidal Silicon Dioxide | Dispersing Agent | 1.9947 | 1–10 | 0.1157 |
| Yellow #6 | Colorant | 0.0934 | <1 | 0.0054 |
| Natural and Artificial Flavors | Flavor | 0.9812 | <1 | 0.0569 |
| Maltodextrin | Diluent/Filler | 31.9050 | 30–40 | 1.8505 |
| Total: | | 100.00% | | 5.8 gm |

The above description is considered that of the preferred embodiment(s) only. Modifications of the invention will occur to those skilled in the art and to those who make or use the invention. Therefore, it is understood that the embodiment(s) described above are merely for illustrative purposes and not intended to limit the scope of the invention, which is defined by the following claims as interpreted according to the principles of patent law, including the doctrine of equivalents.

The invention claimed is:

1. A dispersible dietary fiber powder composition wherein the powder composition consists of a colloidal silicon dioxide; an uncoated, fibrous, vegetable material powder; a saccharide polymer compound; a flavorant; and a preservative.

2. A dispersible dietary fiber powder composition wherein the powder composition consists of a colloidal silicon dioxide and an uncoated, fibrous, vegetable material powder.

3. A dispersible dietary fiber composition wherein the powder composition consists of a colloidal silicon dioxide; an uncoated, fibrous, vegetable material powder; a saccharide polymer compound; and a flavorant.

4. A dispersible dietary fiber composition wherein the powder composition consists of a colloidal silicon dioxide; an uncoated, fibrous, vegetable material powder; and a saccharide polymer compound.

5. The dispersible dietary fiber powder composition of claim 1, wherein the uncoated, fibrous, vegetable material powder comprises less an about 20 mesh (U.S. Series Sieve) particle size.

6. The dispersible dietary fiber powder composition of claim 2, wherein the uncoated, fibrous, vegetable material powder comprises less about 20 mesh (U.S. Series Sieve) particle size.

7. The dispersible dietary fiber powder composition of claim 3, wherein the uncoated, fibrous, vegetable material powder comprises less an about 20 mesh (U.S. Series Sieve) particle size.

8. The dispersible dietary fiber powder composition of claim 4, wherein the uncoated, fibrous, vegetable material powder comprises less han about 20 mesh (U.S. Series Sieve) particle size.

9. The dispersible dietary fiber powder composition of claim 7, wherein the saccharide polymer compound comprises maltodextrin.

10. The dispersible dietary fiber powder composition of claim 8, wherein the saccharide polymer compound comprises maltodextrin.

11. The dispersible dietary fiber powder composition of claim 3, wherein the saccharide polymer compound comprises maltodextrin.

12. The dispersible dietary fiber powder composition of claim 4, wherein the saccharide polymer compound comprises maltodextrin.

13. The dispersible dietary fiber powder composition of claim 11, wherein the maltodextrin comprises a DE (dextrose equivalent) of less than 20.

14. The dispersible dietary fiber powder composition of claim 12, wherein the maltodextrin comprises a DE (dextrose equivalent) of less than 20.

15. The dispersible dietary fiber powder composition of claim 1, wherein the uncoated, fibrous, vegetable material powder comprises an uncoated psyllium powder.

16. The dispersible dietary fiber powder composition of claim 2, wherein the uncoated, fibrous, vegetable material powder comprises uncoated psyllium powder.

17. The dispersible dietary fiber powder composition of claim 3, wherein the uncoated, fibrous, vegetable material powder comprises uncoated psyllium powder.

18. The dispersible dietary fiber powder composition of claim 4, wherein the uncoated, fibrous, vegetable material powder comprises uncoated psyllium powder.

19. The dispersible dietary fiber powder composition of claim 15, wherein the uncoated, fibrous, vegetable material powder comprises less than about 20 mesh (U.S. Series Sieve) particle size.

20. The dispersible dietary fiber powder composition of claim 16, wherein the uncoated, fibrous, vegetable material powder comprises less than about 20 mesh (U.S. Series Sieve) particle size.

21. The dispersible dietary fiber powder composition of claim 17, wherein the uncoated, fibrous, vegetable material powder comprises less than about 20 mesh (U.S. Series Sieve) particle size.

22. The dispersible dietary fiber powder composition of claim 18, wherein the uncoated, fibrous, vegetable material powder comprises less than about 20 mesh (U.S. Series Sieve) particle size.

23. The dispersible dietary fiber powder composition of claim 1, wherein the colloidal silicon dioxide comprises from about 0.5% to about 10% by weight of the composition.

24. The dispersible dietary fiber powder composition of claim 3, wherein the colloidal silicon dioxide comprises from about 0.5% to about 10 by weight of the composition.

25. The dispersible dietary fiber powder composition of claim 3, wherein the colloidal silicon dioxide comprises from about 0.5% to about 10 by weight of the composition.

26. The dispersible dietary fiber powder composition of claim 4, wherein the colloidal silicon dioxide comprises from about 0.5% to about 10 by weight of the composition.

27. The dispersible dietary fiber powder composition of claim 23, wherein the colloidal silicon dioxide comprises from about 1% to about 3% colloidal silicon dioxide and the uncoated, fibrous, vegetable material powder comprises an uncoated psyllium powder.

28. The dispersible dietary fiber powder composition of claim 24, wherein the colloidal silicon dioxide comprises from about 1% to about 3% colloidal silicon dioxide and the uncoated, fibrous, vegetable material powder comprises an uncoated psyllium powder.

29. The dispersible dietary fiber powder composition of claim 25, wherein the colloidal silicon dioxide comprises from about 1% to about 3% colloidal silicon dioxide and the uncoated, fibrous, vegetable material powder comprises an uncoated psyllium powder.

30. The dispersible dietary fiber powder composition of claim 26, wherein the colloidal silicon dioxide comprises from about 1% to about 3% colloidal silicon dioxide and the uncoated, fibrous, vegetable material powder comprises an uncoated psyllium powder.

* * * * *

UNITED STATES PATENT AND TRADEMARK OFFICE
CERTIFICATE OF CORRECTION

PATENT NO. : 7,232,577 B2  
APPLICATION NO. : 10/274803  
DATED : June 19, 2007  
INVENTOR(S) : Hoess et al.

It is certified that error appears in the above-identified patent and that said Letters Patent is hereby corrected as shown below:

Column 6, claim 5, line 10;

"an" should be --than--.

Column 6, claim 6, line 14;

After "less" insert --than--.

Column 6, claim 7, line 18;

"an" should be --than--.

Column 6, claim 8, line 22;

"han" should be --than--.

Column 6, claim 16, line 48;

Before "uncoated" insert --an--.

Column 6, claim 17, line 52;

Before "uncoated" insert --an--.

Column 6, claim 18, line 55;

Before "uncoated" insert --an--.

Column 7, claim 24, line 10;

"claim 3" should be --claim 2--.

UNITED STATES PATENT AND TRADEMARK OFFICE
CERTIFICATE OF CORRECTION

PATENT NO. : 7,232,577 B2
APPLICATION NO. : 10/274803
DATED : June 19, 2007
INVENTOR(S) : Hoess et al.

It is certified that error appears in the above-identified patent and that said Letters Patent is hereby corrected as shown below:

Column 7, claim 24, line 11;

"10" should be --10%--.

Signed and Sealed this

Third Day of June, 2008

JON W. DUDAS
*Director of the United States Patent and Trademark Office*